United States Patent [19]
Longo et al.

[11] Patent Number: 6,102,271
[45] Date of Patent: Aug. 15, 2000

[54] CIRCULAR STAPLER FOR HEMORRHOIDAL SURGERY

[75] Inventors: Antonio Longo, Palermo, Italy; John R. Bittner, Loveland; Randall L. Hacker, Goshen, both of Ohio; Federico Bilotti, Hamburg, Germany

[73] Assignee: Ethicon Endo-Surgery, Inc., Cincinnati, Ohio

[21] Appl. No.: 09/197,805

[22] Filed: Nov. 23, 1998

[51] Int. Cl.[7] .................................................. A61B 17/068
[52] U.S. Cl. ........................ 227/180.1; 227/19; 227/175.1
[58] Field of Search ................................. 227/19, 175.1, 227/180.1, 178.1, 176.1

[56] References Cited

U.S. PATENT DOCUMENTS

| | | | |
|---|---|---|---|
| 348,843 | 9/1886 | Hamilton . | |
| 1,286,083 | 11/1918 | Pennington . | |
| 2,922,415 | 1/1960 | Campagna | 128/4 |
| 4,207,898 | 6/1980 | Becht | 128/305 |
| 4,304,236 | 12/1981 | Conta et al. | 128/325 |
| 4,351,466 | 9/1982 | Noiles | 227/8 |
| 4,603,693 | 8/1986 | Conta et al. | 128/305 |
| 4,834,067 | 5/1989 | Block | 128/4 |
| 5,292,053 | 3/1994 | Bilotti et al. | 227/179 |
| 5,344,059 | 9/1994 | Green et al. | 227/179 |
| 5,392,979 | 2/1995 | Green et al. | 227/179 |
| 5,395,030 | 3/1995 | Kuramoto et al. | 227/19 |
| 5,411,508 | 5/1995 | Bessler et al. | 227/19 |
| 5,522,534 | 6/1996 | Viola et al. | 227/179.1 |

FOREIGN PATENT DOCUMENTS

WO 96/18344 6/1966 WIPO .......................... A61B 17/04

OTHER PUBLICATIONS

Particular Experience with Mechanical Sutures: Circular Stapler for Hemorrhoidectomy, by G. Allegra Giorn Chir. vol. 11 — No. 3 — pp. 95 97, Mar. 1990).

*Primary Examiner*—Scott A. Smith
*Attorney, Agent, or Firm*—Matthew S. Goodwin

[57] ABSTRACT

A circular sapling instrument for the removal of hemorrhoids has a stapling end effector having a casing, a hollow staple driver within the casing, an annular blade having an open distal end is located within the staple driver, and a elongated interior drive shaft is reciprocable within the staple driver and the annular blade. A first inner chamber is defined between the staple driver and the interior drive shaft, and a second inner chamber is defined between the annular blade and the drive shaft. The first chamber communicates with the second chamber. The casing has an exterior surface and a substantially unobstructed passageway extends within the casing surface, into the first inner chamber, into the second inner chamber, and through the open distal end of the second inner chamber for insertion and withdrawal of a surgical instrument therethrough.

6 Claims, 14 Drawing Sheets

CIRCULAR STAPLER FOR HEMORRHOIDAL SURGERY

FIELD OF THE INVENTION

The present invention relates, in general, to circular staplers and, more particularly, to the use of a circular stapler to perform a hemorrhoidectomy.

BACKGROUND OF THE INVENTION

Hemorrhoids are a swollen twisted mass of varicose veins that are located just inside the anus. Hemorrhoids are caused by chronic straining, from constipation, and childbirth. Chronic straining damages the valves located within the veins, and venous blood collects and distends the veins to many times the normal size. The slow flow of blood within the vessel can cause additional injury to the vessel and thrombosis. While rarely fatal, hemorrhoids are painful and treatments can range from heat packs and bed rest (in mild cases), to surgery (in extreme cases). As the patient ages, the elasticity of the tissue of the anus changes and the hemorrhoidal condition can worsen causing prolapse and anal bleeding.

Hemorrhoids can be of two types, external and internal. A ribbed dentate line is located 2.5–3 cm. in from the exterior of the anus and marks the change from the anus to the rectum. External hemorrhoids are found in the anal area below this line and internal hemorrhoids are found in the rectal area above this line. Internal hemorrhoids are generally formed from an internal rectal venous plexus that resides in a submucosal space within the wall of the rectum, approximately 2.5 to 5 cm in from the exterior of the anus. It is a feature of the human anatomy that the venous plexus has three main venous branches or groups located circumferentially around the anus and rectum, and that hemorrhoids usually occur at one or more of these branches. Thus, internal hemorrhoids can protrude from the wall of the rectum in one localized area, more than one localized area, or circumferentially. In severe cases, the internal hemorrhoids can protrude out of the anus.

Internal hemorrhoids are rated by severity from a mild case (first degree) to a much more severe case (fourth degree). First and some second degree cases can be treated by injection or ligation (elastic banding). For the third and fourth degree cases, surgical intervention can be required.

In the past, a wide variety of surgical methods have been suggested for the treatment of severe internal hemorrhoids. The preferred method in the United States is the Ferguson, or closed, hemorrhoidectomy. In the Ferguson procedure, a Ferguson-Hill retractor is inserted into the anus to obtain access to a hemorrhoidal site. The surgeon then clamps the hemorrhoid with alligator clamps, ligates the vessels, and dissects the hemorrhoid from the rectal wall with a scalpel or scissors. Once the hemorrhoid is removed, the surgical site is sutured closed. The retractor is rotated to another position and the remaining hemorrhoids are dealt with in a similar manner.

In general, European surgeons prefer the Milligan-Morgan, or open hemorrhoidectomy for the removal of internal hemorrhoids. In the Milligan-Morgan procedure, rather than using a retractor, the anus is gently dilated with two fingers and forceps are placed at the mucocutaneous junction of each primary hemorrhoid. The hemorrhoids are pulled down and a second forceps is applied to the main bulk of each hemorrhoid to produce "a triangle of exposure". Next, the clamped, hemorrhoid is dissected from the sphincter muscle and is dissected proximally as far as the pedicles and then ligated or tied. Unlike the Ferguson procedure, the wound is not sutured closed, but is left open with a light dressing applied to the wound.

Another hemorrhoidectomy procedure is the Whitehead procedure, which was first performed in 1882. In this procedure, the hemorrhoidal tissue is excised above the dentate line and the redundant rectal mucosa is excised and sutured to the anoderm. This surgery is indicated for circumferential hemorrhoids. Several modifications of Whitehead exist, including raising the anoderm and suturing it to the rectal mucosa. Many surgeons avoid this method as the procedure was thought to be difficult to perform, bloody, and susceptible to complications.

The need for a simple and fast method of performing a hemorrhoidectomy was recognized by Dr. G. Allegra and presented in his 1990 paper entitled "Particular Experience with Mechanical Sutures: Circular Stapler for Hemorrhoidectomy" which was presented to the $1^{st}$. National Conference of the Italian Viscerosynthesis Association in May 28–30, and published in *GIORN Chir*. Vol. 11- No. 3- pp 95–97, March 1990. This report detailed the use of a conventional circular stapler to perform a hemorrhoidectomy on second and third degree hemorrhoids.

In his paper, Dr. Allegra teaches the use of three fingers to dilate the anus and the placement of a continuous submucosal circle of suture at the base of the pectinate or dentate line. Dr. Allegra also underscores the use of a curved needle to place the suture ring submucosally and stresses that the entry and exit point of the suture be the same or nearly the same.

Next, a conventional circular stapling instrument, having a stapling end effector, is opened by amply extending an anvil assembly away from a stapling head assembly. The opened stapling end effector is placed into the anus of a patient and positioned to place the anvil assembly of the stapling end effector distal to the suture ring and the stapling head assembly (of the stapling end effector) proximally outside the patient. This placement enables the surgeon to reach within the anus and to grasp the loose ends of the suture. The loose ends of the suture are drawn out of the anus and out of the stapling end effector between the open anvil and the stapling head assembly. The loose ends of the suture are then pulled upon to draw the circle of suture closed and to draw the anal tissue in around the anvil shaft connecting the open anvil to the stapling head assembly of the circular stapling instrument. Next, the surgeon tightly knots the suture about the anvil shaft and closes the anvil upon the hemorrhoidal mass. The loose ends of the suture protrude from the stapling end effector between the closed anvil and the stapling head assembly. The stapler is fired to perform the hemorrhoidal transection. Once fired, the circular stapling instrument is removed from the anus with the transected hemorrhoids captured within.

The firing of the circular stapler effectively transects the hemorrhoids and applies staples to the transection site. The use of staples as an effective fastening means is well known in bowel surgery, but not as well known in hemorrhoidal surgery. Studies of 10 cases by Dr. Allegra revealed the hemorrhoidal transection occurs at the submucosal level and does not involve the muscular striae. Thus, the Allegra procedure offers surgeons an alternative to conventional hemorrhoidal procedures such as those developed by Ferguson, Milligan-Morgan, and Whitehead.

Whereas Dr. Allegra did indeed pioneer the use of a circular stapler for hemorrhoidal removal, he was limited by the use of a circular stapler that was optimized for bowel surgery. Circular stapling instruments are well known in the surgical art for bowel surgery and an example of such a device is the ECS 25 Endopath™ ILS Endoscopic Curved Intraluminal Stapler from Ethicon EndoSurgery Inc., Cincinnati, Ohio. Many circular stapler patents exist, for example U.S. Pat. No. 4,207,898 by Becht, U.S. Pat. No. 4,351,466 to Noiles, U.S. Pat. No. 5,292,053 to Bilotti et al., and U.S. Pat. 5,344,059 to Green et. al.

One limitation of the Allegra procedure is the depth that the circular stapler can be placed into the anus. As described above, the open anvil assembly of the stapling end effector is placed distal to the suture ring and the stapling head assembly is placed proximally outside the patient. This enables the surgeon to grasp the loose ends of the suture and to draw the suture out of the anus through the gap between the anus and the stapling head assembly. The need for the gap to withdraw the suture from the anus limits the depth that the stapling end effector can be placed into the anus. If the hemorrhoids are located deeper into the anal canal, such as internal hemorrhoids, the stapling head assembly enters the anus and effectively blocks the surgeon from accessing the loose ends of the suture. What is needed is a circular stapling instrument that is not limited to external hemorrhoids but can access hemorrhoids wherever they exist. Such an instrument could effectively be used for the removal of internal hemorrhoids above the dentate line.

An additional limitation of the Allegra procedure is the amount of hemorrhoidal tissue that can be drawn into the stapling end effector of a conventional circular stapling instrument. Hemorrhoids are drawn into and around an anvil shaft (connecting the open anvil assembly to the stapling head assembly) by tightening a continuous loop of suture placed below the dentate line. This action draws the hemorrhoids around the anvil shaft but does not draw the hemorrhoids into the inner chamber of the stapling head assembly. This limits the amount of hemorrhoidal tissue that can be brought into the stapling end effector and the surgeon may remove part of a hemorrhoid. What is needed is a method of drawing the hemorrhoids around the anvil shaft and into the inner chamber of the stapling head assembly to ensure that more of the hemorrhoidal tissue is removed in a single firing of the circular stapling instrument.

Whereas Dr. Allegra describes the use of fingers to dilate the anus during placement of sutures into the hemorrhoidal area, this procedure is tiring and difficult at best. What is needed is a means of dilating the anus during suture placement that does not require the use of a surgeons hand. This would reduce the number of hands required for the surgery and speed up the suturing process. One such means is the use of an anoscope, or speculum, such as those described by Hamilton in U.S. Pat. No. 348,843, by Pennington in U.S. Pat. No. 1,286,083, by Campagna in U.S. Pat. No. 2,922,415, and by Block in U.S. Pat. No. 4,384,067. Whereas these anoscopes were indeed an aid to surgery, they generally provide a pistol grip handle for the surgeon to grasp. The Hamilton patent teaches a pair of generally adjacent handles available for the operation of the instrument. One handle is fixed to the anoscope and is gripped by the surgeon in a pistol grip like manner for rotation of the anoscope within the patient. The second handle is attached to a rotating sleeve within the anoscope, and rotational movement of the handle and the sleeve effectively opens or closes an access slot extending longitudinally down the anoscope body. What is needed is an anoscope that does not provide a pistol grip handle and has an improved handle to facilitate the suturing of the hemorrhoids.

At present, there are no known surgical instruments that can meet all of the needs outlined above. These and other advantages will become more apparent from the following detailed description and drawings.

SUMMARY OF THE INVENTION

Accordingly, the present invention is a circular stapling instrument adapted for the removal of internal hemorrhoids. The instrument comprises a handle, a shaft extending from the handle, and a stapling head assembly extending from the shaft.

The stapling head assembly has a substantially hollow casing having an exterior casing surface. A substantially hollow staple driver is received in the casing for movement therein between a prefired position and a fired position. An annular blade is mounted within the staple driver at a distal end of the staple driver. An elongated interior drive shaft is reciprocable within the staple driver and the annular blade.

An anvil assembly has an anvil shaft attached to the elongated interior drive shaft. The anvil assembly is movable in response to reciprocation of the interior drive shaft from an open position spaced from the casing to a closed position adjacent to the casing. When the anvil assembly is in the open position, the staple driver and the interior drive shaft define a first inner chamber therebetween.

When said staple driver is in the prefired position, a substantially unobstructed passageway is provided. The passageway extending from the exterior casing surface of the casing into the first inner chamber for insertion and withdrawal of a surgical instrument into and from the first inner chamber.

According to the present invention, when the anvil assembly is in the open position, the annular blade and the interior drive shaft define a second inner chamber therebetween. The second inner chamber communicates with the first inner chamber. When the staple driver is in the prefired position, the passageway extends from the exterior casing surface of the casing into the second inner chamber for insertion and withdrawal of the surgical instrument into and from the second inner chamber.

When the anvil assembly is open, the second inner chamber has an open distal end so that the passageway extends from the exterior casing surface of the casing and through the open distal end of the second inner chamber for insertion and withdrawal of a surgical instrument therethrough. Additionally when the anvil assembly is closed, the second inner chamber has a closed distal end.

In a preferred embodiment of the present invention, the casing has a casing surface aperture extending from a flared casing portion of the casing surface to an outer tubular casing portion of the casing surface. The driver has a driver surface aperture extending from a flared driver portion of the driver surface to an outer tubular driver portion of the driver surface. When the staple driver is received in the casing and the staple driver is in the prefired position, the casing surface aperture is aligned with the driver surface aperture.

Significantly, the unobstructed passageway extending from the exterior casing surface into the first and second inner chambers of the circular stapling instrument of this invention appreciably facilitates the surgical removal of deep, internal hemorrhoids by enabling the surgeon to pass instruments though the passageway to grasp and draw the hemorrhoidal tissue into the stapling instrument for stapling and eventual removal.

The circular stapling instrument of this invention can be used in open and endoscopic surgical procedures, but it is particularly adapted for use during a surgical hemorrhoidectomy procedure.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE PREFERRED EMBODIMENTS

The present invention is a novel surgical instrument for the removal of tissue from a human patient. More particularly, the invention concerns the use of an improved circular stapling instrument for the removal of internal hemorrhoids.

Figure 1:
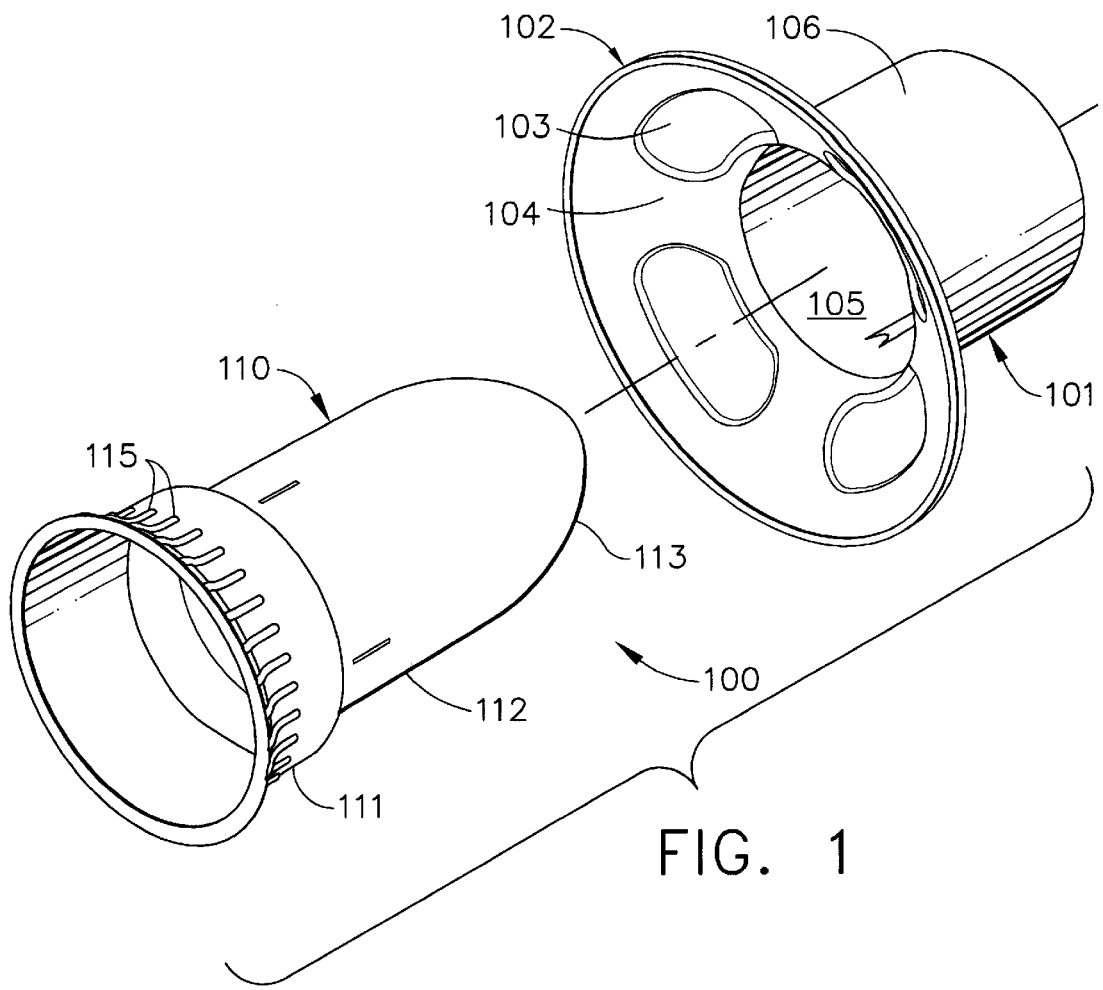
FIG. 1 is an exploded isometric view of an anal introducer for use with the preferred circular stapling instrument of this invention during hemorrhoid removal surgery.

Turning now to FIG. 1, an anal introducer 100 is shown in an exploded view. The anal introducer 100 is placed into the anus of a patient to establish an access port through which the hemorrhoidectomy can be practiced. The anal introducer 100 has two components; an anal cannula 101, and an anal obturator 110.

The anal cannula 101 has a proximal dished flange 102, a distal cannula sleeve 106, and a cannula bore 105 extending therethrough. The dished flange 102 has four equally spaced suture apertures 103 located therein. The apertures 103 are provided so that the surgeon can suture the dished flange 102 of the anal cannula 101 to the patient once the access port is established (FIG. 8).

The anal obturator 110 is an elongated cylindrical obturator that has a distal atraumatic tip 113, an elongated shaft 112, and a proximal grip 111. Prior to surgery, the anal obturator 110 is inserted into the cannula bore 105 of the above anal cannula 101 to form the assembled anal introducer 100 (FIG. 8).

Figure 8:
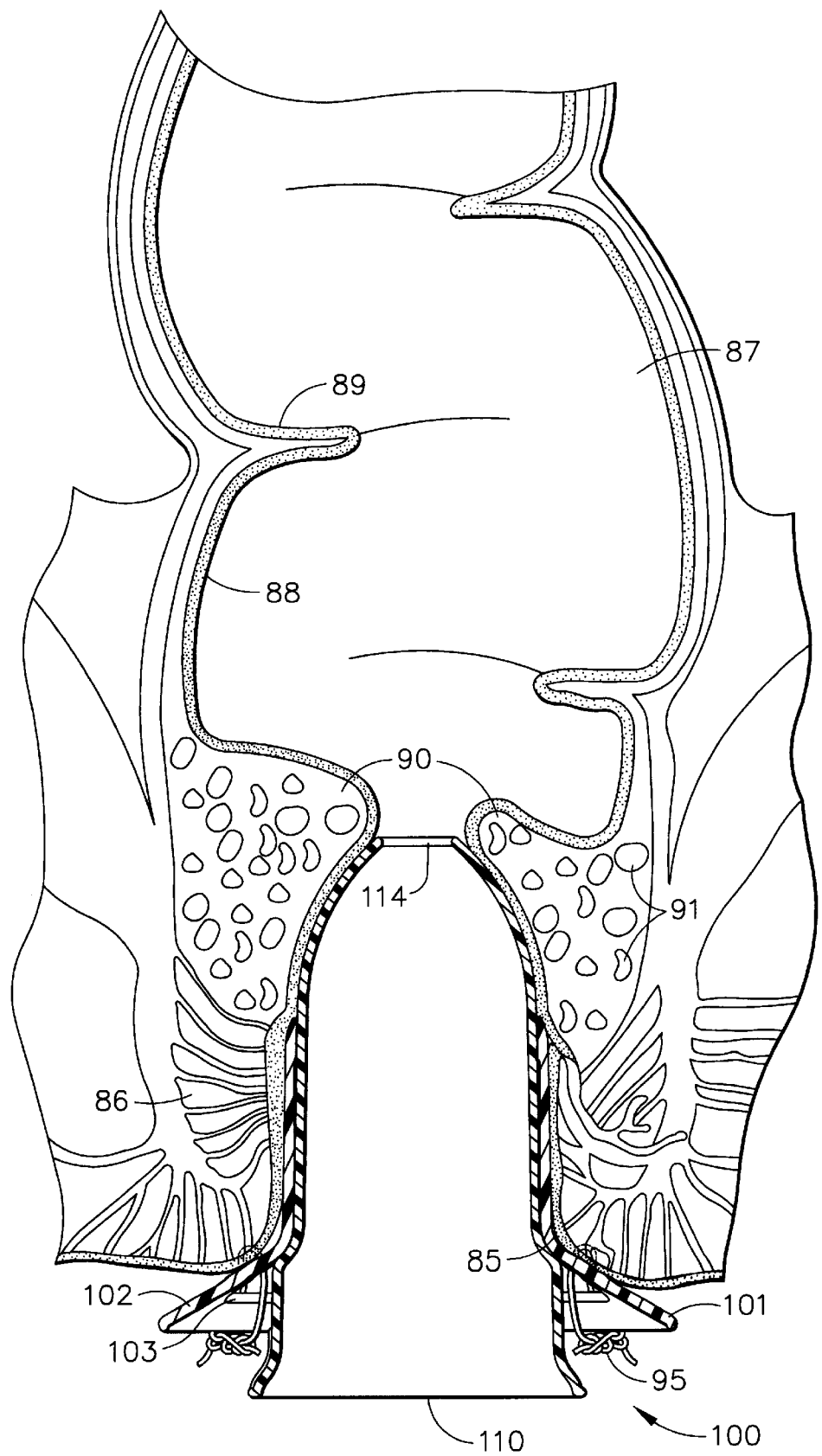
FIG. 8 is a cross sectional view of the anal introducer of FIG. 1 shown inserted into the anus of a patient wherein the anal cannula of the anal introducer is sutured in position.

Once assembled, the atraumatic tip 113 of the anal obturator 110 protrudes beyond the distal end of the anal cannula 101 (FIG. 8). The grip 111 extends proximally beyond the dished flange 102 and has a plurality of equally spaced ribs 115 to increase the surgeon's grasp upon the anal introducer 100. The surgeon grasps the anal introducer 100 by the grip 111 and inserts the rounded atraumatic tip 113 into the anus of the patient to gently dilate and obturate the anal sphincter. The anal introducer 100 is inserted until the dished flange 102 is in contact with the patient. The anal cannula 101 and the anal obturator 110 are constructed from any of a wide variety of engineering thermoplastics including polycarbonate, polystyrene and the like.

Figure 2:
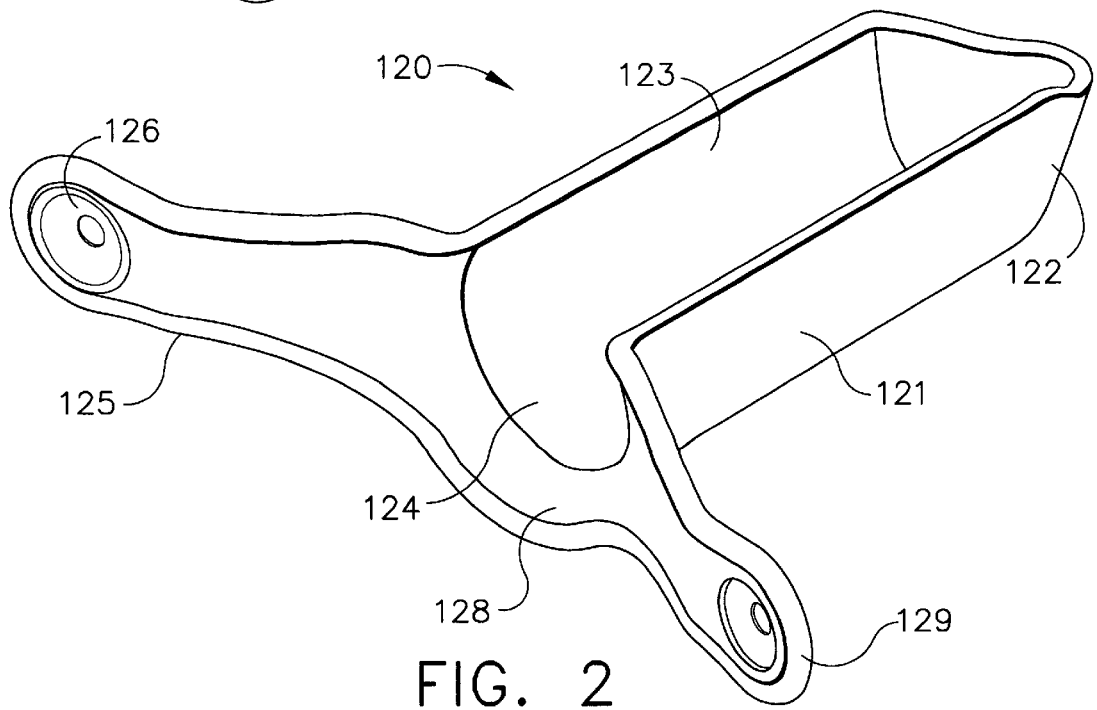
FIG. 2 is an isometric view of an anoscope for use in combination with the anal introducer depicted in FIG. 1.
Figure 3:
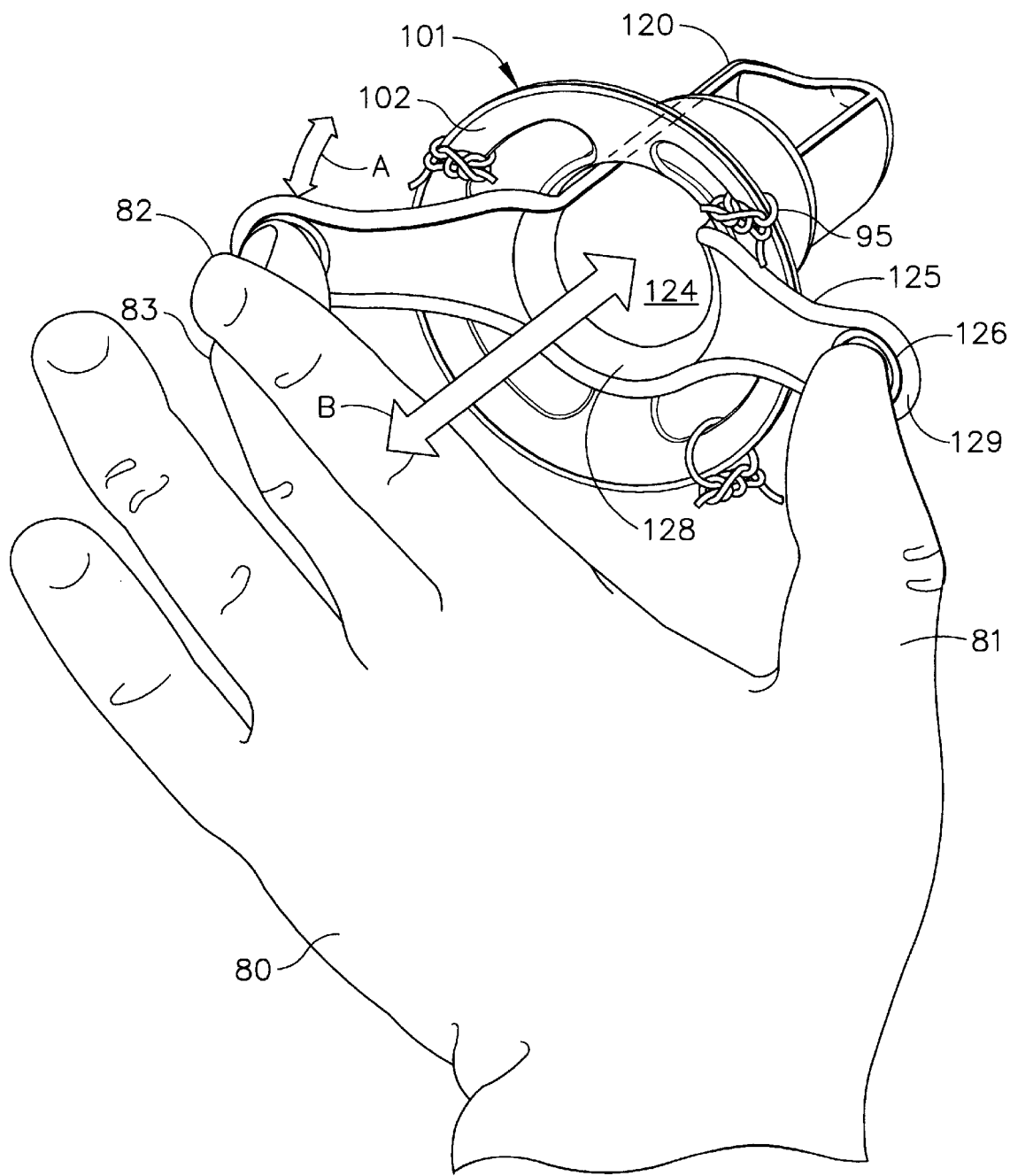
FIG. 3 is an isometric view of the anoscope of FIG. 2 showing the anoscope inserted into an anal cannula of the anal introducer of FIG. 1, wherein the anal cannula is placed into an anus of the patient (removed for clarity) and the anoscope is being manipulated by the middle finger and the thumb of a surgeon's hand.
Figure 16:
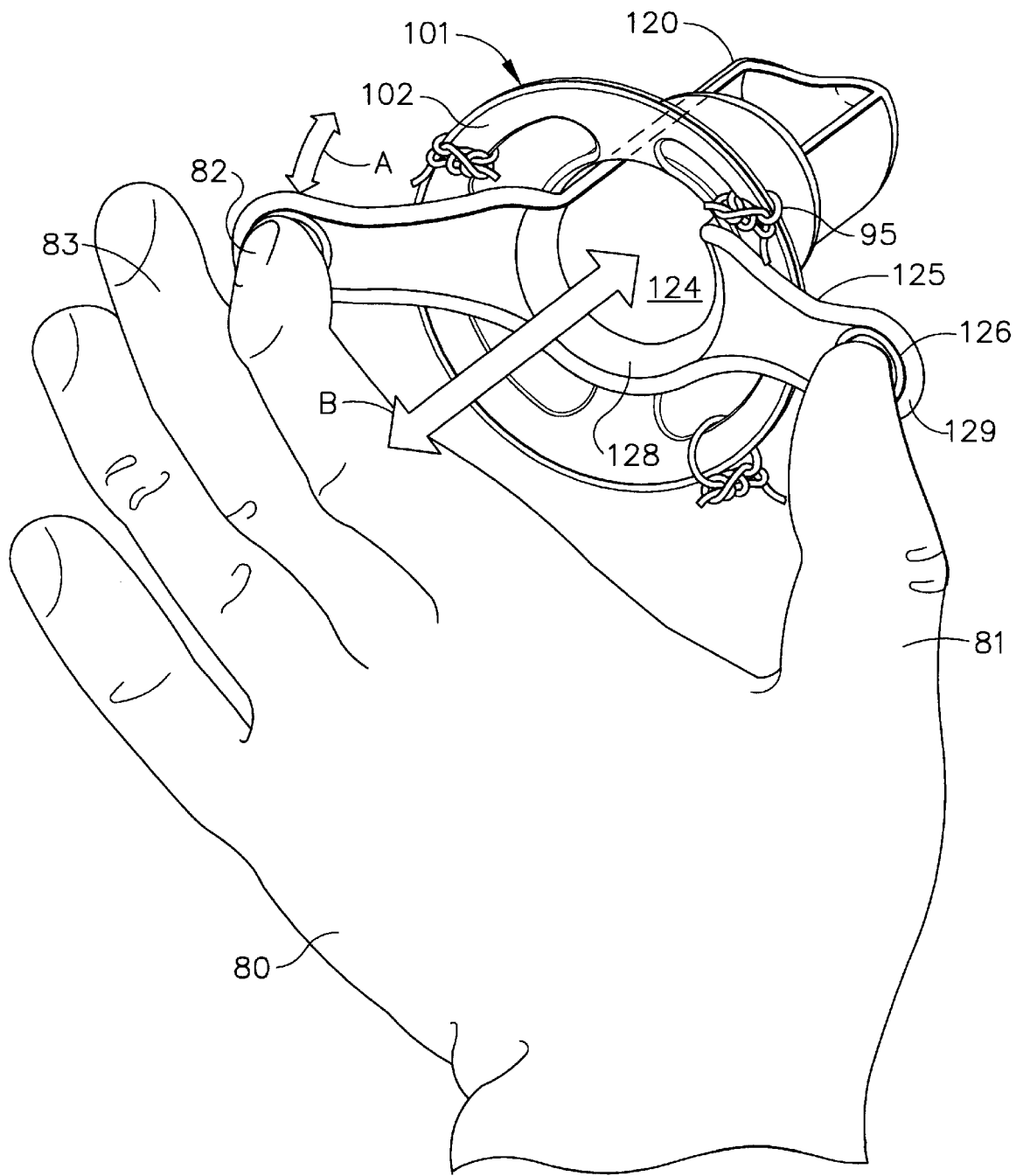
FIG. 16 is similar to that of FIG. 3 wherein the improved anoscope is being manipulated by the index finger and the thumb of a surgeon's hand.

Turning now to FIGS. 2 and 3, the improved anoscope 120 is shown free standing in FIG. 2 and in use in FIG. 3. FIG. 2 shows the anoscope 120 as being substantially symmetrical about the longitudinal axis and having a distal conical tip 122 to provide atraumatic obturation of the anal canal. A channel body 121 extends proximally from the distal conical tip 122 and defines an anoscope bore 124 for the introduction of surgical instruments or tools. A flange 128 is radiused outward from the channel body 121. A slot 123 is formed within the channel body 121 and extends from the distal conical tip 122, through the flange 128, and communicates with the anoscope bore 124. A pair of mutually opposed finger wings 125 are for manipulation and rotation of the anoscope 120. The finger wings extend from the flange 128 and flank the slot 123. The finger wings 125 are specifically formed into an arch to fit within the dished flange 102 of the anal cannula 101 for free rotation of the anoscope 102 (FIG. 3). The finger wings 125 have a pair of finger wing tips 129. Each finger wing tip 129 has a concave surface 126 embedded within for the insertion of a finger of a user. The concave surfaces 126 have at least one texture ring located therein to reduce slippage of a finger when the finger is placed into one of the concave surfaces 126. The shape of the finger wings 125 and the spacing apart of the concave surfaces 126 are such that the surgeon can easily rotate the anoscope 120 with one hand and perform the surgical procedure with the other (FIG. 3, arrow A). The concave surfaces 126 are located adjacent to the ends of the finger wings 125 and are appropriately spaced for the reception of a thumb 81 and a middle finger 82 within (FIG. 3). When the anoscope is in use (FIG. 3), this spacing places the "V" formed between the index finger 82 and the thumb 81 of the surgeon's hand below and to the side of the anoscope bore 124 and frees up the surgeon's index finger 82 for use during the surgery. It is also possible to place the thumb 81 and the index finger 82 within the concave surfaces 126 (FIG. 16) to optimally place the "V" formed between the index finger 82 and the thumb 81 to position the hand such that surgical instruments can be easily inserted and withdrawn into the anoscope 120 over the hand as shown by arrow B in FIG. 16.

Figure 4:
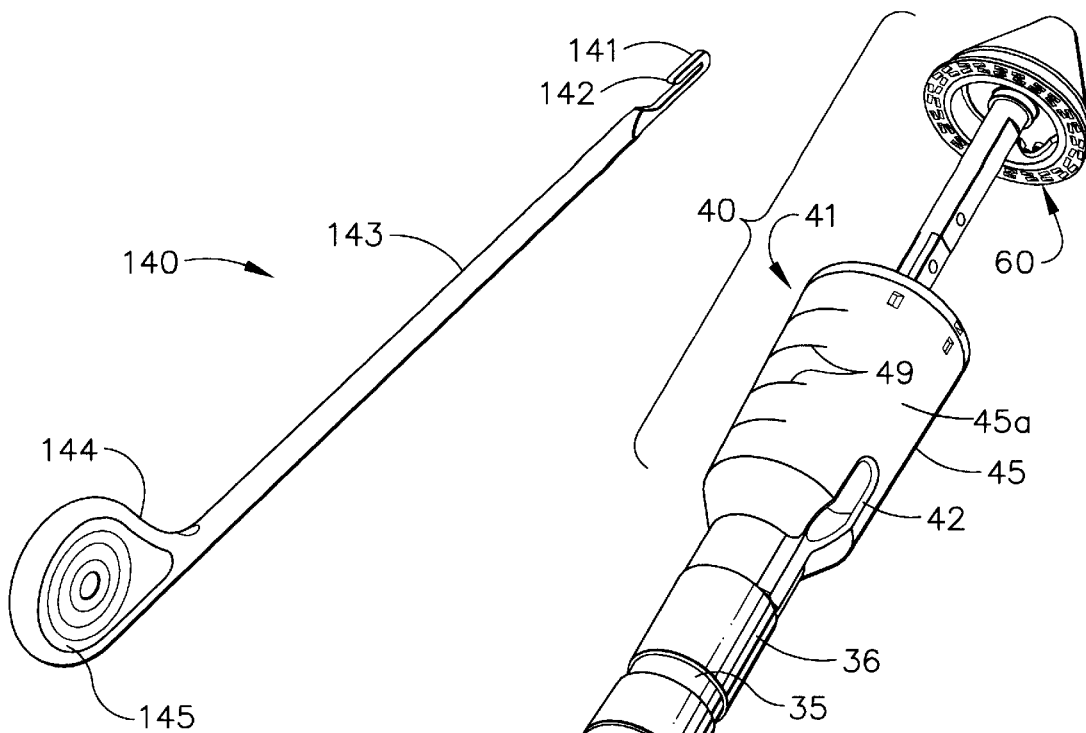
FIG. 4 is an isometric view of a surgical instrument for engaging suture during hemorrhoid removal surgery using the preferred circular stapling instrument of FIG. 5.

Focussing now on FIG. 4, there is illustrated a surgical instrument 140 for engaging suture that is particularly adapted for use with the circular stapling instrument 25 as will be described below. The surgical instrument 140 has a proximal grip 144 for the surgeon to grasp, an elongated shaft 143, and a distal suture end effector 141 for the engagement of suture. The grip 144 has raised grip features 145 to enhance the surgeon's grasp upon the surgical instrument 140. The suture end effector 141 is rounded to provide a blunt atraumatic surface during surgery and a suture hook 142 for the entrapment of suture 26.

Figure 5:
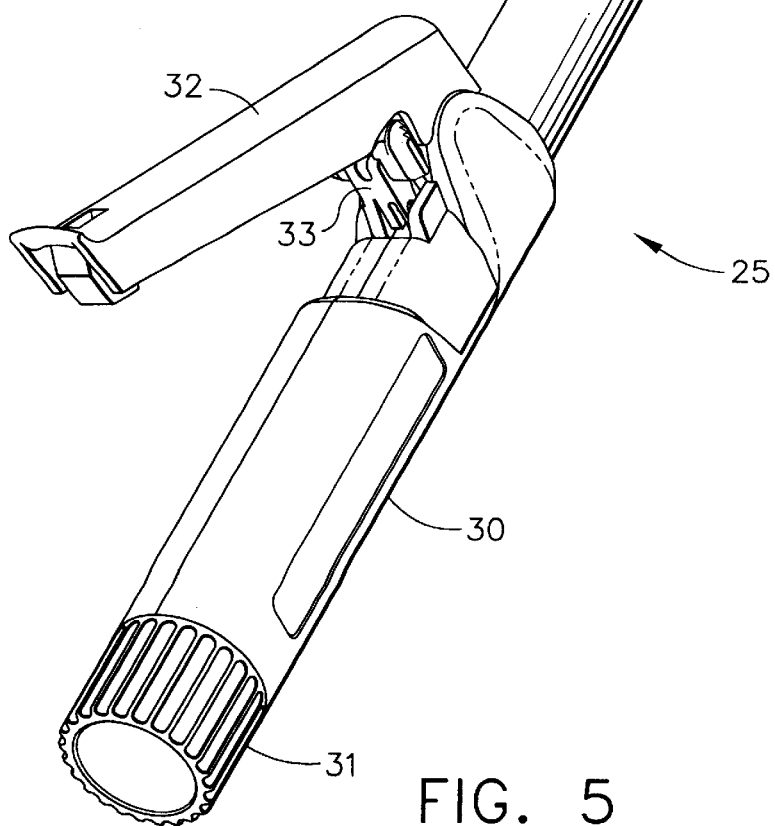
FIG. 5 is an isometric view of the preferred surgical stapling instrument for hemorrhoidal removal, wherein the anvil is shown in the open position.
Figure 6:
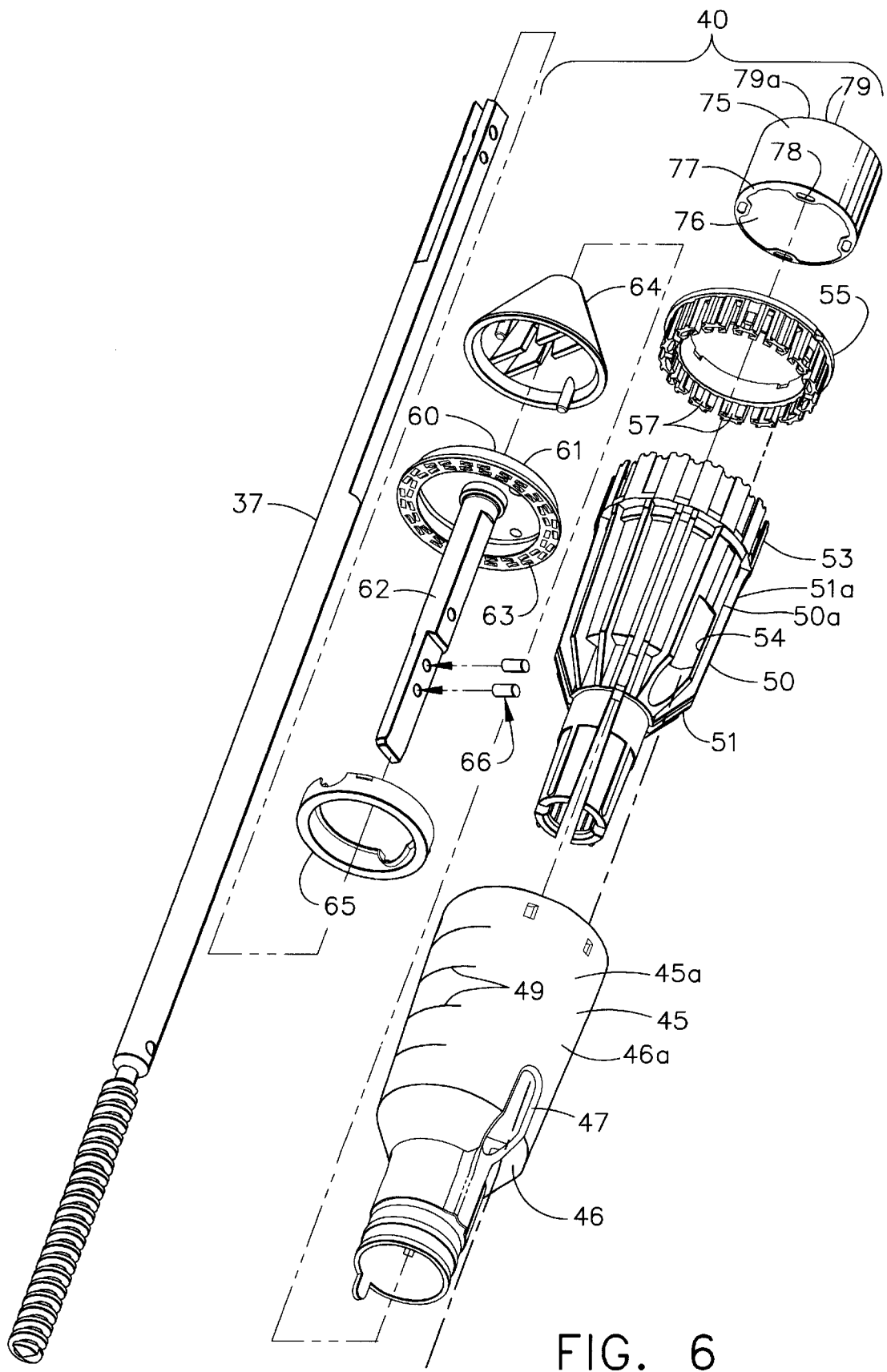
FIG. 6 is an exploded isometric view of the stapling end effector of the preferred surgical stapling instrument of FIG. 5.
Figure 7:
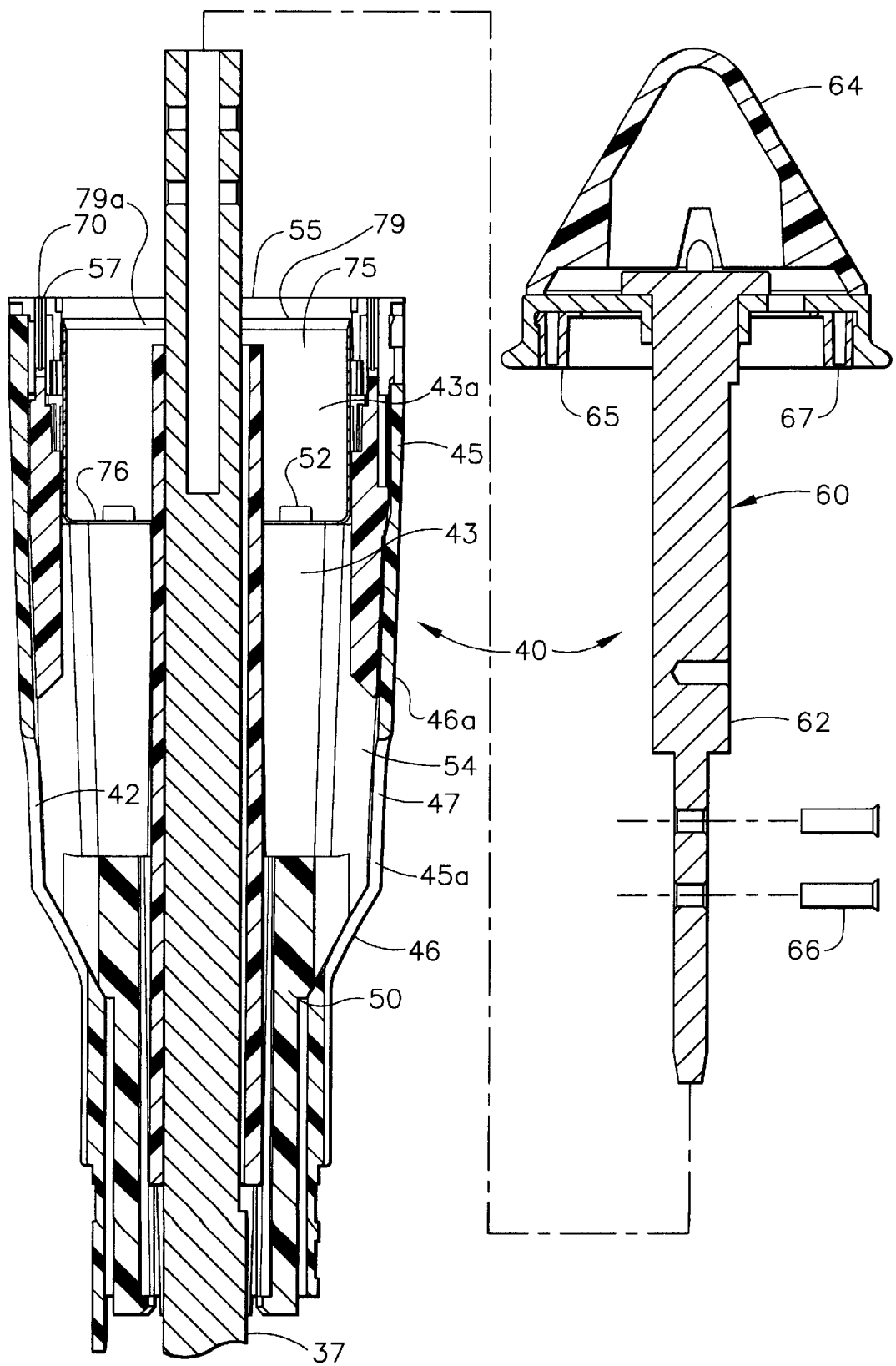
FIG. 7 is a plan elevational view, in cross section, of the stapling end effector of the preferred surgical stapling instrument of FIG. 5 wherein the attached anvil assembly is shown disassembled from the stapling head for clarity.

Turning now to FIGS. 5–7, a preferred circular stapling instrument 25 for the removal of internal hemorrhoids is shown. The circular stapling instrument 25 has been adapted from a conventional circular stapling instrument (not shown) and has a stapling end effector 40 adapted to place an annular array of staples into a mucosal layer 88 (FIG. 8) at the base of at least one inner hemorrhoid 90 (FIG. 8) and to cut the inner hemorrhoid 90 from the inside wall of the rectum 87 or anus 85. The conventional circular stapling instrument is generally used to anastomose two sections of bowel together with an annular ring of staples, and cuts a plug from the center of the annular formed staple ring for the passage of fecal material. The conventional circular stapling instrument is not especially adapted for hemorrhoidal removal.

Turning now to FIG. 5, the improvements made to the circular stapler 25 include an ergonomically shortened shaft 35, an enlarged stapling head assembly 41 capable of receiving a larger amount of tissue within (FIG. 7), a plurality of guide marks 49 located upon an outer casing 40 of the stapling head assembly 41 to provide anal insertion depth information, an anvil assembly 60 attached to a reciprocating drive shaft 37 (FIG. 6) of an anvil opening mechanism (not shown) to prevent accidental removal of the anvil assembly 60, and most significantly, a pair of opposed passageways 42 extending into the stapling head assembly 41. These passageways 42 will be described in much greater detail below.

Like the conventional circular stapling instruments, the preferred circular stapling instrument 25 has a handle 30. An anvil closure knob 31 is located on the proximal end of the handle 30 and is operatively coupled to the anvil assembly 60 such that rotation of the knob 31 moves the anvil assembly 60 proximally or distally, depending on the direction of rotation of the knob 31. A firing trigger 32 is movable from an open position to a closed position (not shown) to form staples into hemorrhoidal tissue and to cut the hemorrhoidal tissue with the stapling end effector 40. A safety latch 33 is located beneath the firing trigger 32 and is shown in the up position which prevents closure of the firing trigger 32. When the safety latch 33 is rotated down. The firing trigger 32 is free to move from the open position to the closed position. These operations will be described in greater detail below.

Figure 13:
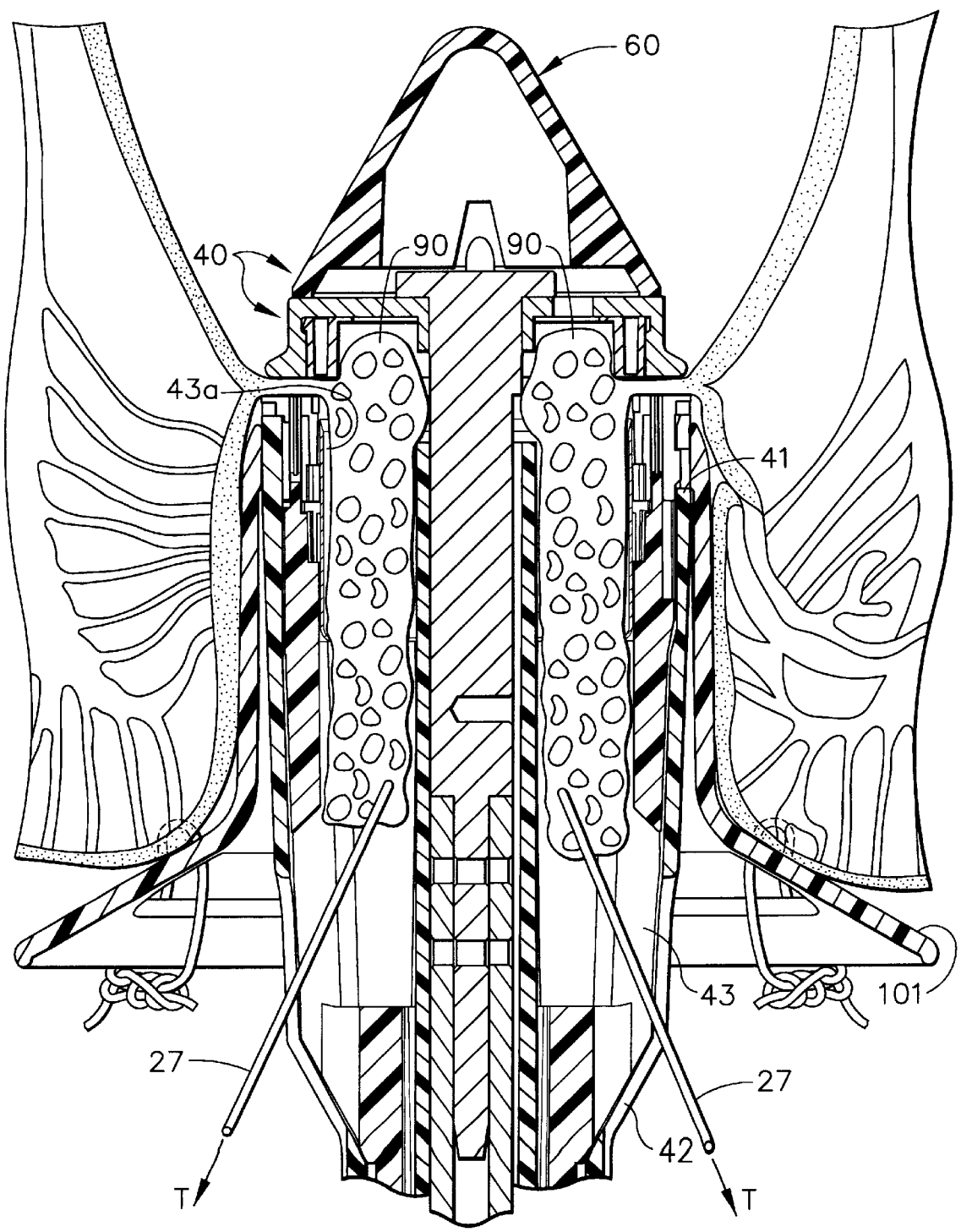
FIG. 13 is similar to that of FIG. 11, but with the purse string suture drawn tight to draw the hemorrhoids into the inner chamber of the stapling end effector whereupon the anvil of the stapling end effector is closed upon the hemorrhoids prior to the firing of the preferred surgical stapling instrument.

The shaft 35 extends distally from the handle 30 and is shortened to ergonomically place the handle 30 closer to the anal surgical site. The stapling head assembly 41 is conventionally attached to the shaft 35 with a ferrule 36. The anvil assembly 60 is shown in the open position in FIG. 5 and is movable to a closed proximal position adjacent to a hollow casing 45 of the stapling head assembly 41 (FIG. 13).

FIG. 6 shows an exploded view of the stapling head assembly 41 of FIG. 5. Whereas the stapling head assembly 41 is similar to those used on conventional circular stapling instruments, there are important differences that will be pointed out to the reader below. The hollow casing 45 of the stapling head assembly 41 is fixedly mounted to the shaft 35 by the ferrule 36 (FIG. 5). The hollow casing 45 has an exterior surface 45a having a flared driver portion 46 and an outer tubular driver portion 46a. The passageways 42 (FIG. 5) described above have a casing surface aperture 47 extending from the flared driver portion 46 to the outer tubular portion 46a. An annular staple holder 55 is mounted within a distal end of the hollow casing 45 and has an annular array of staple slots 57.

A substantially hollow staple driver 50 is movably mounted within the casing 45 and has a plurality of fingers 53 that are received within the staple slots 57 within the staple holder 55. The fingers 53 are for engaging and driving a plurality of staples 70 from the staple slots 57 of the staple holder 55 as the hollow staple driver 50 is moved from a prefired position to a fired position by actuation of the firing trigger 32. The staple driver 50 has an exterior driver surface 50a having a flared driver portion 51 and an outer tubular driver portion 51a. A pair of open driver surface apertures 54 extend from the flared driver portion 51 to the outer tubular driver portion 51a. When the staple driver 50 is mounted within the casing 45, the driver surface apertures 54 are aligned with the casing surface apertures 47 to form the substantially unobstructed passageways 42. The substantially unobstructed passageways 42 formed from the driver surface apertures 54 and the casing surface apertures 47 are generally parallel to the interior drive shaft 37.

A cup shaped annular blade 75 is mounted within the distal end of the staple driver 50 and is attached by a plurality of blade mounting pins 52 that project through a like number of mounting holes 78 within a base 77 of the annular blade 75. The annular blade 75 moves with the staple driver 50 and has a large blade opening 76 within the base. The open distal end 79 has a cutting edge 79a.

The elongated interior drive shaft 37 is located within the stapling head assembly 41 and is reciprocable within the staple driver 50 and the annular blade 75.

The anvil assembly 60 has an anvil shaft 62 that is attached to the distal end of the drive shaft 37 by a pair of rivets 66 and is operatively connected to the anvil closure knob 31 as described above. A disk shaped anvil 61 is attached to the distal end of the anvil shaft 62 and has a circular array of staple forming pockets 63 imprinted into the proximal surface of the disk. An anvil shroud 64 is attached to the distal end of the anvil 61 and an annular breakaway washer 65 mounts within the disk of the anvil 60 adjacent to the staple forming pockets 63. The anvil assembly 60 is movable from an open position for the reception of hemorrhoidal tissue to a closed position adjacent to the stapling head assembly 41 to clamp hemorrhoidal tissue within. When the anvil assembly is closed, the staples 70 are formed within the anvil pockets 63 as they are ejected from the staple holder 55 and tissue is cut by the circular blade 75 against the breakaway washer 65. When the anvil assembly 60 is in the open position, the passageways 42 extend from the exterior casing surface 45a, through the first inner chamber 43, through the second inner chamber 43a, and through the open distal end 79 of the annular blade 75. When the anvil assembly 60 is in the closed position adjacent to the stapling head assembly 41, the open distal end 79 of the annular blade 75 is closed and the passageways 42 extend from the exterior casing surface 45a and through the first inner chamber 43 and into the second inner chamber 43a.

Turning now to FIG. 7, when the staple driver 50 is in the prefired position a first inner chamber 43 is generally formed between the hollow staple driver 50 and the interior drive shaft 37. The passageways 42 extend within the stapling head assembly 41 from the exterior casing surface 45a and communicate with the first inner chamber 43. A second inner chamber 43a is generally defined between the annular blade 75 and the interior drive shaft 37. The second interior chamber 43a has an open distal end 79. The first chamber 43 and the second chamber 43a communicate through the blade opening 76. The passageways 42 extends from the exterior casing surface 45a through the first inner chamber 43, through the second inner chamber 43a, and through the open distal end 79 of the annular blade 75.

Turning now to the section views of FIGS. 8–13, there is shown a series of steps for using the above surgical instruments (singly and in combination) for the removal of internal hemorrhoids 90 from a human patient. The surgical method pictured in FIGS. 8–13 is performed upon a patient suffering from a severe case of internal hemorrhoids 90. The internal hemorrhoids 90 are enlarged around the entire anal circumference and are located above the dentate line 92. Removal of the internal hemorrhoids 90 is indicated.

Looking at FIG. 8, the assembled anal introducer 100 is shown inserted within the anus 85 of the patient. Prior to the view shown in FIG. 8, the atraumatic tip 113 (FIG. 1) of the anal obturator 110 was placed against the exterior of the anus 85, and with an application of pressure to the grip 111 (FIG. 1), the anal introducer 100 was inserted into the anus 85 of the patient to dilate the sphincter muscle 86. The insertion continued until the until the dished flange 102 of the anal cannula 101 was stopped by contact with the patient. A series of retaining sutures 95 were placed through the suture apertures 103 of the anal cannula 101 and into the anus 85 of the patient, and tied to prevent expulsion of the anal cannula 101 from the anus 85. The anal obturator 110 is shown pushing the internal hemorrhoids 90 upwards into the rectum 87. An opening 114 is provided in the anal obturator 110 to prevent a vacuum from forming within the anus 85 and rectum 87 as the anal obturator 110 is removed.

Figure 9:
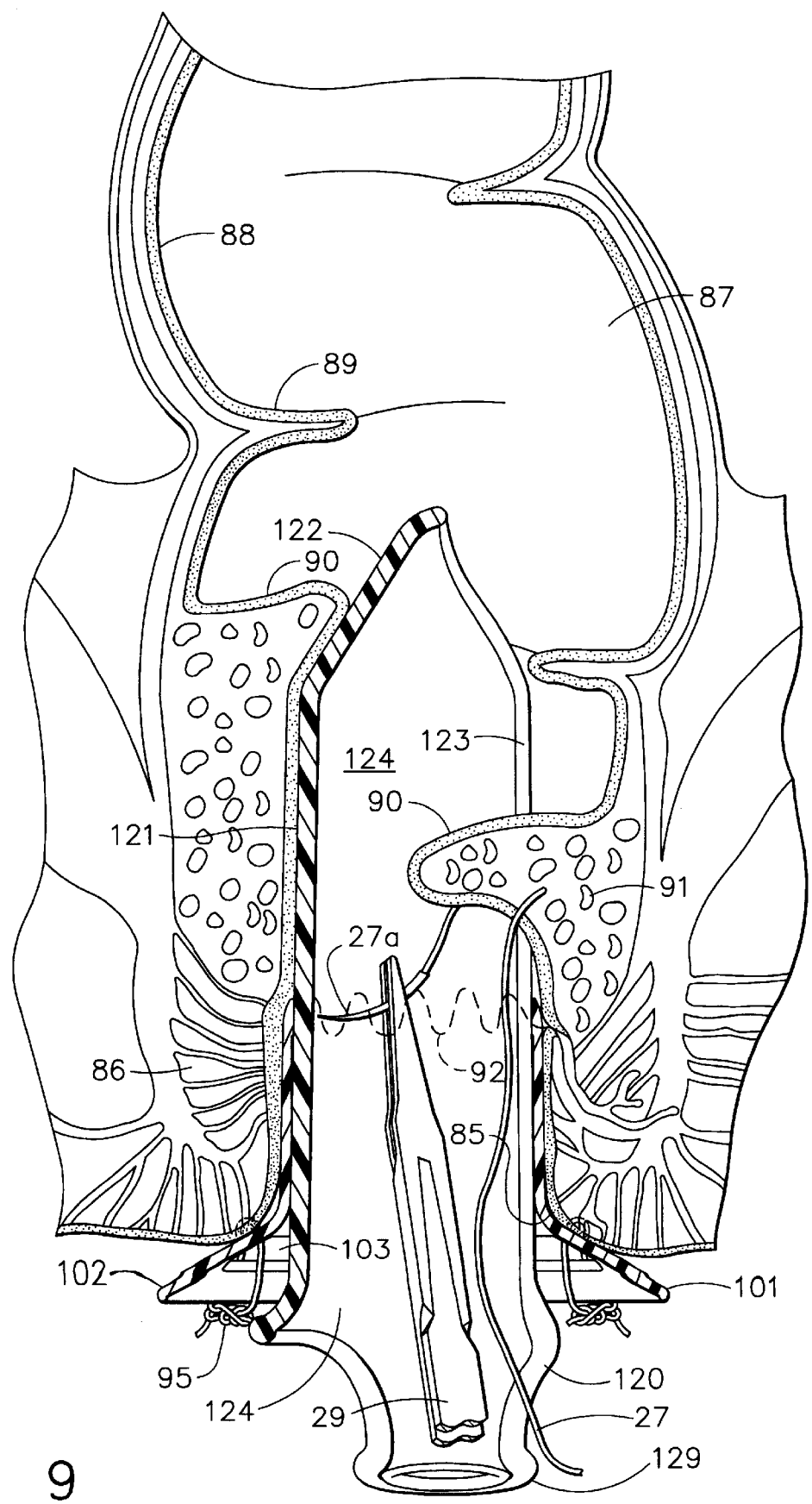
FIG. 9 is similar to that of FIG. 8, but with the anoscope of FIG. 2 inserted into the cannula of the anal introducer of FIG. 1 and showing a surgical forceps applying a purse string suture to a hemorrhoid of the patient.

Referring now to FIG. 9, the anal obturator 110 has been removed from the anal cannula 101 and the anoscope 120 has been fully inserted into the cannula bore 106 (FIG. 1) of the anal cannula 101. The surgeon has rotated the anoscope 120 to position the slot 123 in alignment with the right hemorrhoid 90. The swollen vascular mass of the right internal hemorrhoid 90 is protruding into the anoscope bore 124. The left hemorrhoid 90 is in contact with the exterior of the channel body 121 and the channel tip 122. The surgeon is in the process of placing a purse string suture 27 into the right hemorrhoid using a needle grasper 29. The reader is advised to note that the purse string suture 27 is being placed into an internal hemorrhoid 90 well above a dashed dentate line 92 which extends horizontally behind the channel body 121. Once the purse string suture 27 is placed into the first internal hemorrhoid 90, the anoscope 120 is rotated to continues until all the internal hemorrhoids 90 are sutured and the loose ends of the continuous purse string suture 27 are drawn close together. At this time, the needle 27a is removed (by cutting) and the anoscope 120 is removed from the patient.

Figure 10:
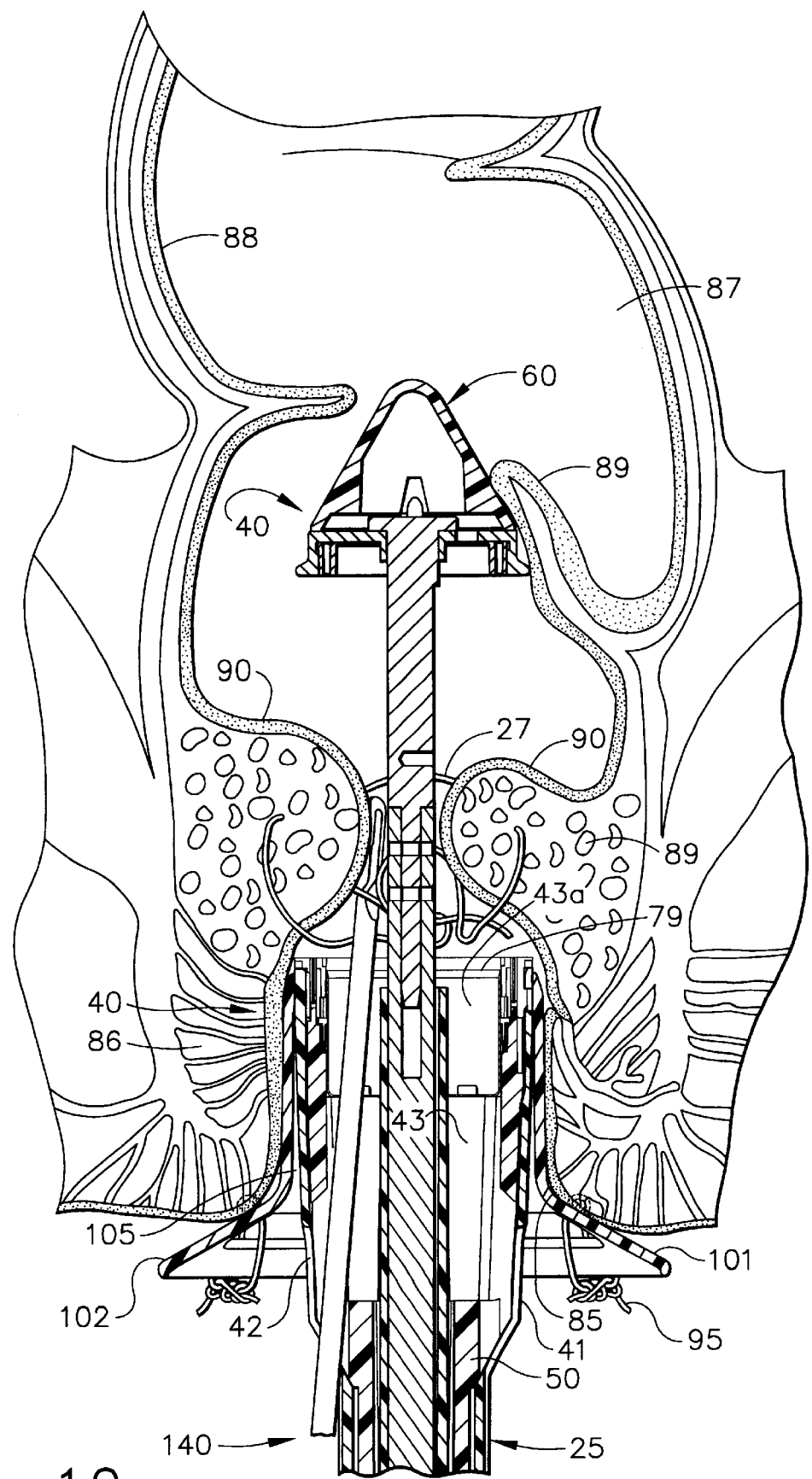
FIG. 10 illustrates the stapling end effector of the preferred surgical stapling instrument of FIG. 5 in the open position inserted into the cannula of the anal introducer of FIG. 1 with the surgical instrument for engaging suture of FIG. 3 shown inserted into the passageway of the stapling end effector to engage the loose ends of the purse string suture.
Figure 11:
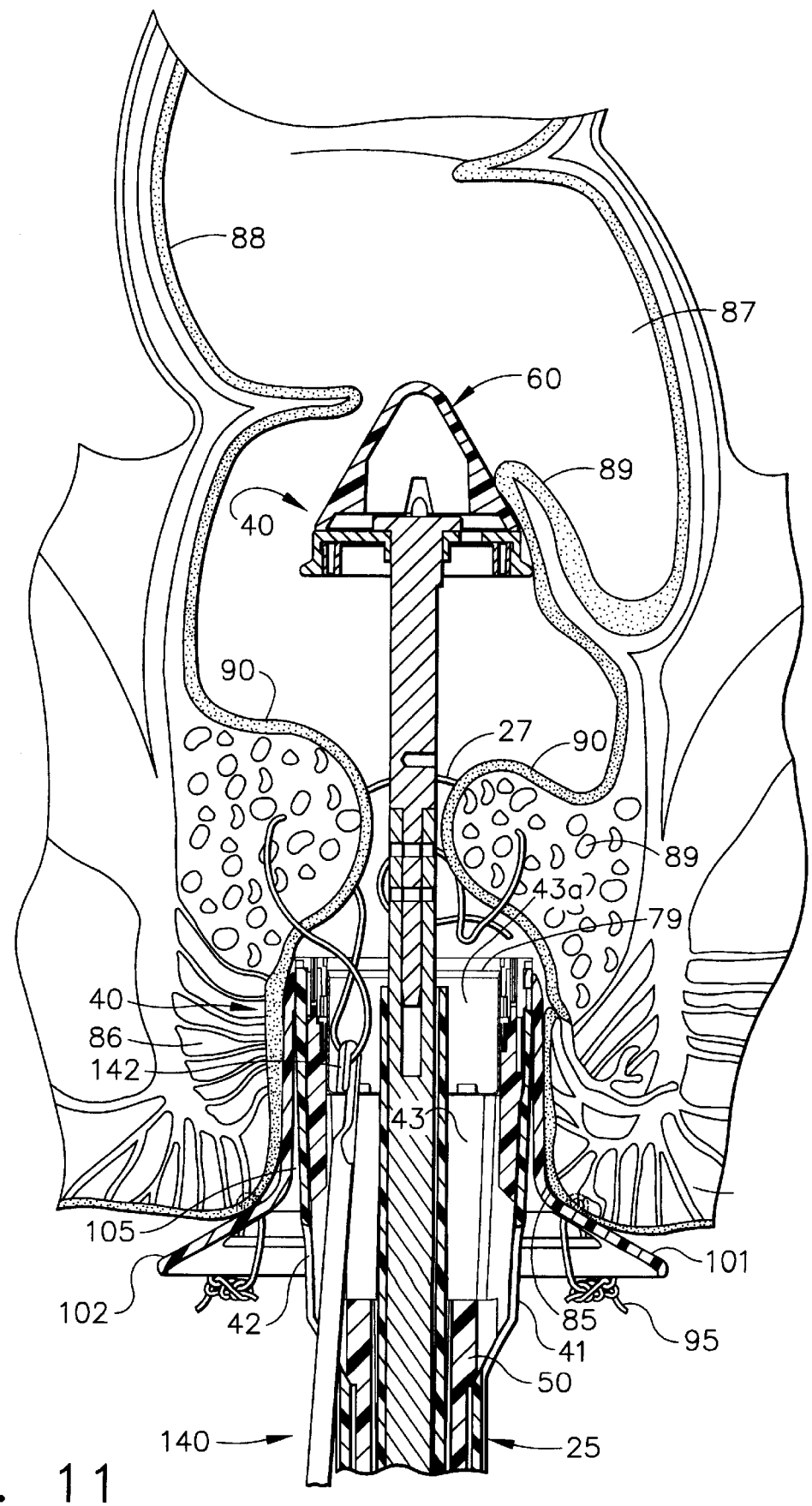
FIG. 11 is similar to that of FIG. 10, but with the loose ends of the purse string suture drawn into an inner chamber of the stapling end effector by the surgical instrument for engaging suture.
Figure 12:
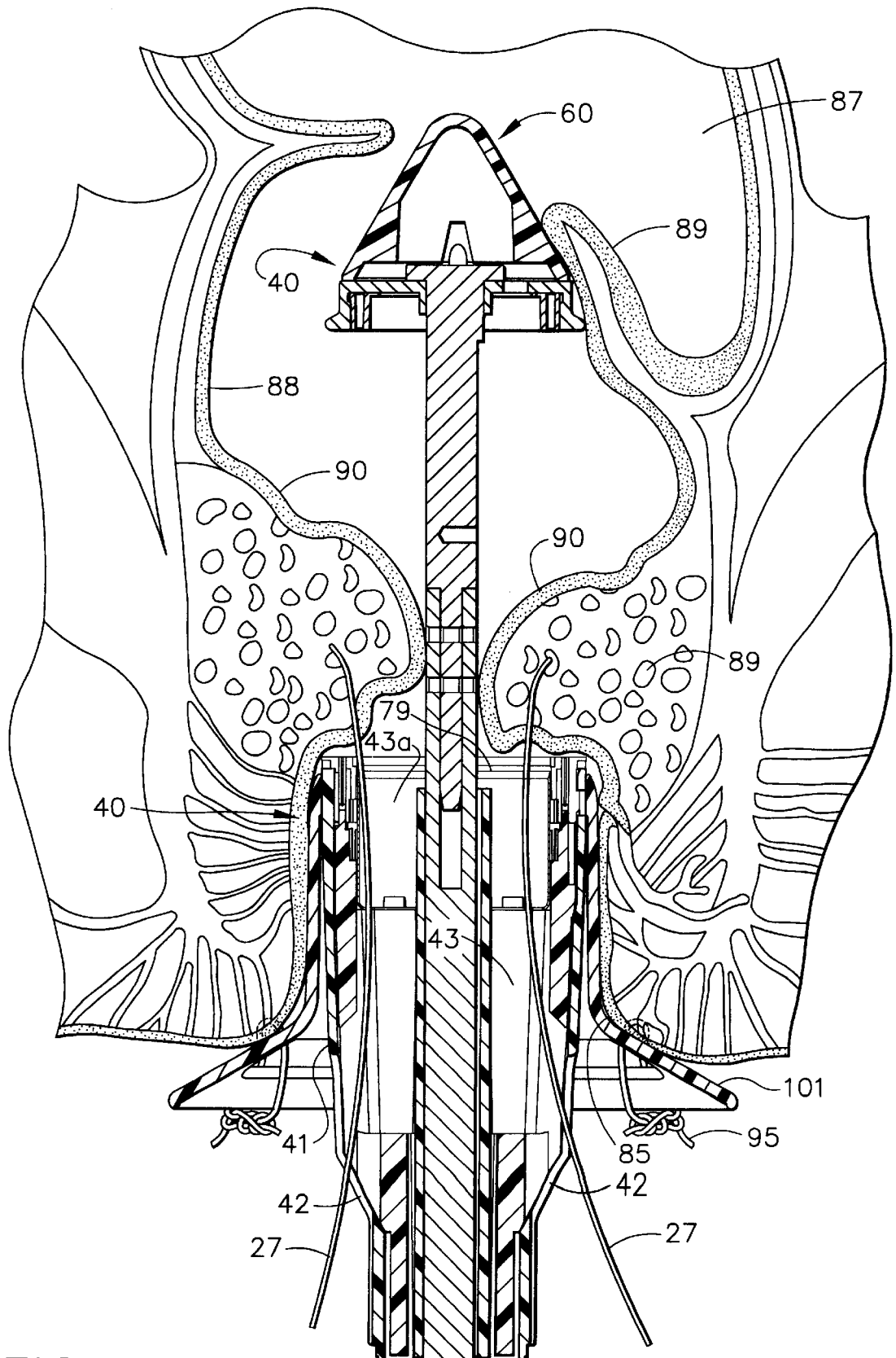
FIG. 12 is similar to that of FIG. 10, but with the loose ends of the purse string suture drawn out of the inner chamber and passageway within the stapling end effector by the surgical instrument for engaging suture.

Turning now to FIGS. 10, 11, and 12, the stapling end effector 40 (FIG. 5) is shown with the anvil assembly 60 open and inserted into the anus 85 and rectum 87 of the patient. The stapling end effector 40 is positioned within the anus such that the purse string suture 27 and the internal hemorrhoids 90 are located between the stapling head assembly 41 and the open anvil assembly 60. The open anvil assembly is inserted into the rectum 87 and is shown displacing a rectal valve 89 upwards. With this particular patient, the internal hemorrhoids 90 are located deep within the patient and this has necessitated the positioning of both the open anvil assembly 60 and the stapling head assembly 41 into the anus 85 of the patient. As shown, the stapling head assembly 41 effectively blocks the surgeon's view of the purse string suture 27 and makes the following step more difficult.

The surgeon must next place the surgical instrument 140 for grasping suture into one of the passageways 42 within the stapling head assembly 41 to engage at least one loose end of the purse string suture 27. In the preferred embodiment, the surgical instrument 140 has a suture hook 142 for engaging the suture. The loose ends of the purse string suture 27 are withdrawn out of the passageway 42 and out of the stapling head assembly 41 with the surgical instrument 140. As shown in FIG. 10, the surgical instrument 140 has been inserted into the left hand passageway 42, through the first inner chamber 43, through the second inner chamber 43a, and through the open distal end 79 of the annular blade 75 to engage the purse string suture 27 distally from the open distal end of the second inner chamber 43a, e.g. between the stapling head assembly 41 and the open anvil assembly 60. It is of note that the circular stapling instrument 25 and the surgical instrument 140 each have a longitudinal axis, and when the surgical instrument 140 is within the passageway 42, the longitudinal axis of the surgical instrument 140 is generally parallel with the longitudinal axis of the circular stapling instrument 25.

Turning now to FIG. 11, the surgical instrument 140 has engaged a loose end of the purse string suture 27 and is shown in the process of drawing the loose end of the suture 27 downward through the second inner chamber 43a. In FIG. 12, the surgeon has drawn both loose ends of the purse string suture 27 out of the passageways 42 and out of the patient. The reader is advised to note that it is the passageways 42 that extend from the exterior casing surface 45a, through the first inner chamber, through the second inner chamber 43a, and through the open distal end 79 of the annular blade 75 that enables the surgeon to engage and draw the loose ends of the purse string suture 27 out of stapling end effector 40 (and the patient) and into the surgeon's grasp. Whereas the loose ends of the purse string suture 27 are shown untied, as a matter of surgeon preference, the loose ends of the purse string suture 27 can be tied together to form a loop.

Referring now to FIG. 13, the hemorrhoids 90 are shown drawn into the first inner chamber 43 and the second inner chamber 43a by the surgeon pulling (proximal to distal) upon the loose ends of the purse string suture 27, or as indicated above, the tied loop of suture. The direction of the pull or tension T applied to the loose ends of the purse string suture 27) is indicated by arrows. Pulling on the loose ends of the purse string suture 27 draws the internal hemorrhoids 90 inward around the open anvil shaft 62 (FIG. 11) and most importantly, simultaneously pulls the drawn internal hemorrhoids 90 into the open distal end 79 of the annular blade 75, into the second inner chamber 43a, and into the first inner chamber 43 of the stapling head assembly 41. The reader is advised to note that with conventional circular staplers, the surgeon is only able to draw hemorrhoids around the anvil shaft of the stapler.

As the surgeon maintains the tension T upon the purse string suture 27 with one hand, he moves the anvil assembly 60 from the open position spaced away from the stapling head assembly 41 to the closed position adjacent to the stapling head assembly 41 to clamp the internal hemorrhoids 90 between the stapling head assembly 41 and the anvil assembly 60. Once the anvil assembly 60 is closed, the surgeon releases the tension T upon the suture 27 and fires the circular stapling instrument 25 to staple and cut the internal hemorrhoids.

Figure 14:
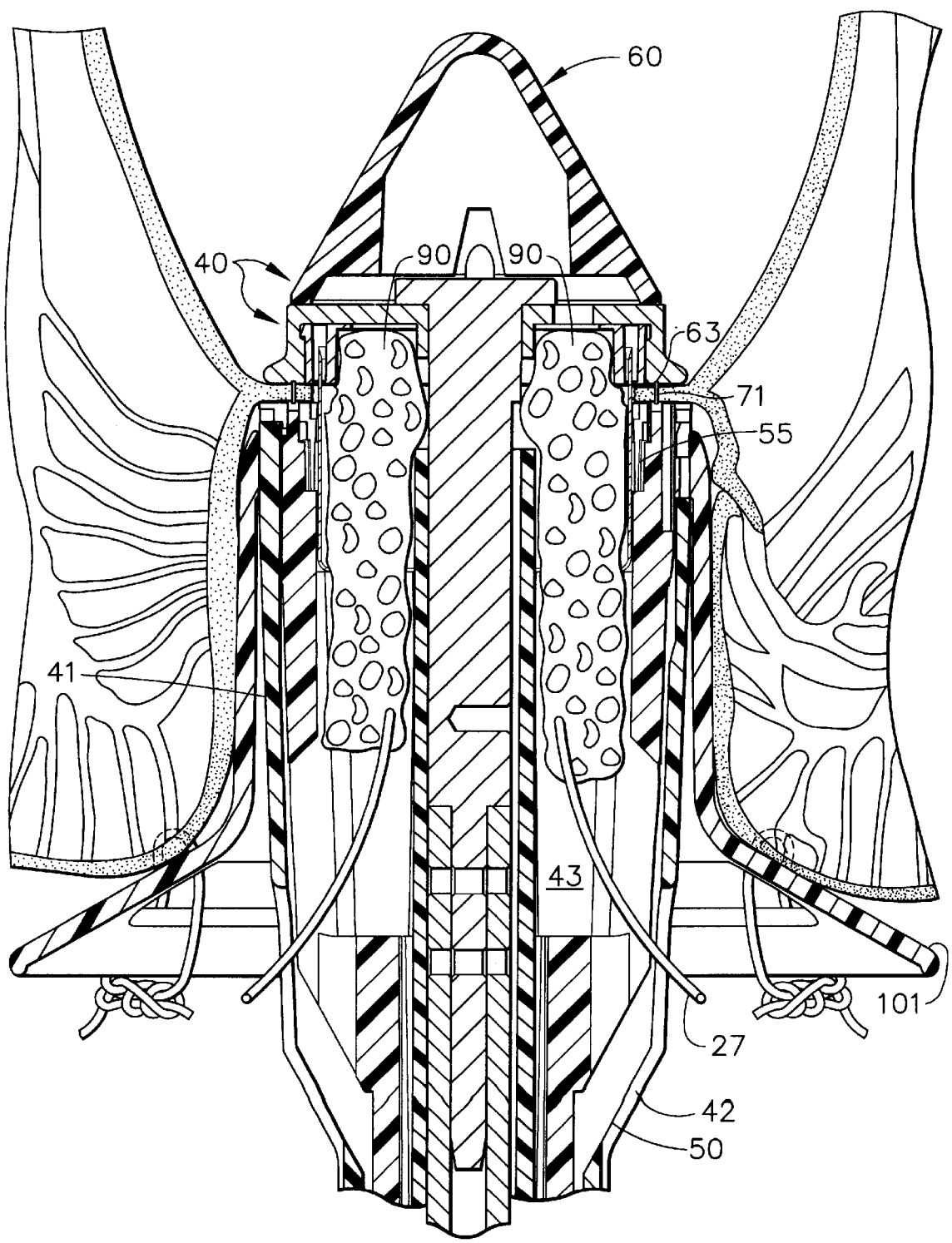
FIG. 14 is similar to that of FIG. 13, wherein the preferred surgical stapling instrument has been fired to place a plurality of staples in the submucosal layer and to sever the hemorrhoidal tissue.

Turning now to FIG. 14, the stapling end effector 40 is shown after the preferred circular stapling instrument 25 (FIG. 5) has been fired. An annular array of staples 70 are expelled from the staple holder 25 (by an upward motion of the staple driver 50) into the portions of the internal hemorrhoids 90 compressed between the anvil assembly 60 and the staple holder 55, and into the staple forming pockets 63 (FIG. 6) of the anvil assembly 60. This action forms the staples 70 into "B" shaped formed staples 71 within the compressed internal hemorrhoids 90. Simultaneously, with the staple formation, the annular blade 75 severs the internal hemorrhoids 90 adjacent to the formed staples 71. To remove the circular stapler from the patient, the surgeon must first open the anvil assembly 60 to release the compressed stapled mucosal tissue from the stapling end effector 40 and then carefully remove the stapling end effector 40 from the anus of the patient (not shown). This procedure leaves the patient with the hemorrhoids removed and a hemostatic ring of staples at the site from whence the hemorrhoids were removed.

Figure 15:
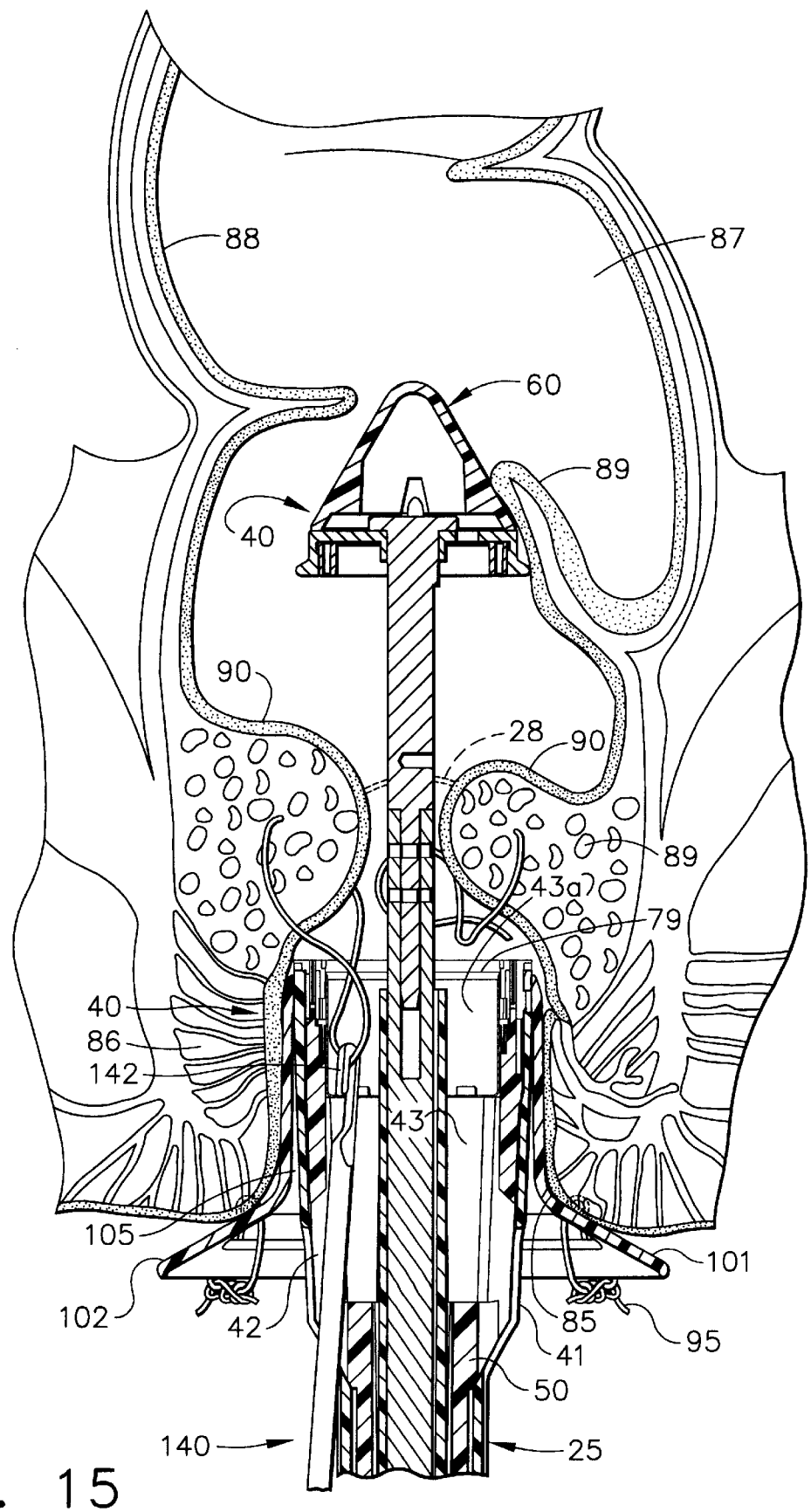
FIG. 15 is similar to that of FIG. 11, but with the surgical instrument for engaging suture of FIG. 4 shown inserted into a passageway within the preferred stapling end effector to engage the loose ends of a continuous circle of suture.

Turning now to FIG. 15, an alternate embodiment of placing a suture 26 into the internal hemorrhoids is shown. The surgeon is shown placing a continuous circle of suture 28 circumferentially about the anus 85 of the patient or the rectum 87 of the patient. The continuous circle of suture 28 is shown being placed below a mucosal layer 88 prior to the insertion of the open circular stapling instrument 45 into the anus 85 of the patient.

The preferred embodiment of the surgical stapling instrument 25 can be supplied to the surgeon as a component in a surgical kit for the removal of hemorrhoids. The kit should contain at least one surgical stapling instrument 25 of the present embodiment in combination with other surgical devices such as anal introducers 100, anoscopes 120, surgical instruments 140 to engage suture, suture 26, and the like. Also, in another embodiment, it is possible to provide a surgical kit having a conventional circular stapler in combination with the other surgical devices listed above.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A circular stapling instrument adapted for the removal of internal hemorrhoids, said instrument comprising:
   a handle;
   a shaft extending from said handle;
   a stapling head assembly extending from said shaft, said assembly having:
   a) a substantially hollow casing having an exterior casing surface,
   b) a substantially hollow staple driver received in said casing for movement therein between a prefired position and a fired position,
   c) an annular blade mounted within said staple driver at a distal end of said staple driver,
   d) an elongated interior drive shaft reciprocable within said staple driver and said annular blade;
   an anvil assembly having an anvil shaft attached to said elongated interior drive shaft, said anvil assembly movable in response to reciprocation of said interior drive shaft from an open position spaced from said casing to a closed position adjacent to said casing, and when said anvil assembly is in the open position, said staple driver and said interior drive shaft define a first inner chamber therebetween, and said annular blade and said interior drive shaft define a second inner chamber therebetween, said second inner chamber communicating with said first inner chamber; and
   wherein when said staple driver is in the prefired position, a substantially unobstructed passageway is provided, said passageway extending from said exterior casing surface of said casing into said first and second inner chambers for insertion and withdrawal of a surgical instrument into and from said first and second inner chambers, said passageway being substantially parallel to said interior drive shaft.

2. The instrument of claim 1 wherein said exterior casing surface has a flared casing portion and an outer tubular casing portion, said staple driver has an exterior driver surface, said exterior driver surface has a flared driver portion and an outer tubular driver portion, and said passageway includes: a) a casing surface aperture extending from said flared casing portion to said outer tubular casing portion, and b) a driver surface aperture extending from said flared driver portion to said outer tubular driver portion, wherein when said staple driver is received in said casing and said staple driver is in the prefired position, said casing surface aperture and said driver surface aperture are aligned with each other.

3. The instrument of claim 1 wherein said second inner chamber has an open distal end when said anvil assembly is in the open position, and when said anvil assembly is in the open position, said passageway extends from said exterior casing surface of said casing through the open distal end of said second inner chamber for insertion and withdrawal of said surgical instrument therethrough.

4. The instrument of claim 3 wherein said second inner chamber has a closed distal end when said anvil assembly is in the closed position.

5. The instrument of claim 3 wherein said passageway is for the withdrawal of a suture through the open distal end of the second inner chamber and out of said passageway within said exterior casing surface.

6. The instrument of claim 3 wherein said passageway is for the passage of suture, said suture moving from a first proximal position within said passageway to a second distal position within said passageway for the drawing of hemorrhoids into the open distal end of said second inner chamber and into said first chamber.

\* \* \* \* \*